(12) United States Patent
Lee

(10) Patent No.: US 10,241,160 B2
(45) Date of Patent: Mar. 26, 2019

(54) MAGNETIC RESONANCE IMAGING APPARATUS AND CONTROL METHOD THEREOF

(71) Applicant: SAMSUNG ELECTRONICS CO., LTD., Suwon-si (KR)

(72) Inventor: Dae Ho Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 816 days.

(21) Appl. No.: 14/704,054

(22) Filed: May 5, 2015

(65) Prior Publication Data
US 2016/0018503 A1  Jan. 21, 2016

(30) Foreign Application Priority Data
Jul. 18, 2014  (KR) .................. 10-2014-0090898

(51) Int. Cl.
*G01R 33/28* (2006.01)
*A61B 5/055* (2006.01)

(52) U.S. Cl.
CPC .......... *G01R 33/283* (2013.01); *A61B 5/0555* (2013.01)

(58) Field of Classification Search
CPC .................. G01R 33/283; G01R 33/546; G01R 33/5673; G01R 33/307; G01R 33/5608; G01R 33/34092; G01R 33/385; A61B 5/0555
See application file for complete search history.

(56) References Cited

U.S. PATENT DOCUMENTS

| | | | |
|---|---|---|---|
| 6,774,929 B1 * | 8/2004 | Kopp | A61B 5/055 345/8 |
| 2005/0283068 A1 * | 12/2005 | Zuccolotto | A61B 5/0555 600/410 |
| 2006/0074305 A1 * | 4/2006 | Mostafavi | A61B 6/032 600/428 |
| 2007/0167724 A1 | 7/2007 | Gadagkar et al. | |
| 2011/0230755 A1 * | 9/2011 | MacFarlane | A61B 5/055 600/414 |
| 2012/0268124 A1 * | 10/2012 | Herbst | G01R 33/56509 324/309 |
| 2013/0021034 A1 * | 1/2013 | Heismann | A61B 5/742 324/318 |
| 2013/0208249 A1 * | 8/2013 | Kimmlingen | G03B 21/14 353/30 |

(Continued)

FOREIGN PATENT DOCUMENTS

| KR | 10-2014-0049916 A | 4/2014 |
|---|---|---|
| KR | 10-2014-0058313 A | 5/2014 |
| KR | 1020140062014 A | 5/2014 |

OTHER PUBLICATIONS

Communication dated Oct. 16, 2015 by the Korean Intellectual Property Office in related Application No. 10-2014-0090898.

(Continued)

*Primary Examiner* — Jeff Natalini
*Assistant Examiner* — Dustin Dickinson
(74) *Attorney, Agent, or Firm* — Sughrue Mion, PLLC

(57) ABSTRACT

A magnetic resonance imaging (MRI) apparatus includes a gantry including a bore, and an image output screen configured to rotate around the bore and output visual information to an object placed in the bore.

23 Claims, 18 Drawing Sheets

(56) References Cited

U.S. PATENT DOCUMENTS

2013/0345543 A1* 12/2013 Steibel, Jr. ............. A61B 6/467
600/407

OTHER PUBLICATIONS

Communication dated Feb. 13, 2018, issued by the Korean Intellectual Property Office in corresponding Korean Application No. 10-2014-0090898.
Communication dated Dec. 4, 2017, issued by the Korean Intellectual Property Office in corresponding Korean Application No. 10-2014-0090898.

* cited by examiner

MAGNETIC RESONANCE IMAGING APPARATUS AND CONTROL METHOD THEREOF

CROSS-REFERENCE TO RELATED APPLICATION

This application claims priority from Korean Patent Application No. 10-2014-0090898, filed on Jul. 18, 2014, in the Korean Intellectual Property Office, the disclosure of which is incorporated herein in its entirety by reference.

BACKGROUND

1. Field

Apparatuses and methods consistent with exemplary embodiments relate to a magnetic resonance imaging (MRI) apparatus, and a control method thereof.

2. Description of the Related Art

Medical imaging apparatuses acquire information of a patient and provide the information as an image. The medical imaging devices include an ultrasonic diagnostic device, an X-ray tomography device, a magnetic resonance imaging (MRI) device, etc. Among these devices, the magnetic resonance imaging apparatus provides excellent contrast in soft tissues and various diagnostic information images, thus being widely used in the medical imaging field.

The magnetic resonance imaging apparatus images a human body by converting energy discharged from atomic nuclei into a signal by supplying a designated frequency and energy to atomic nuclei in a state in which a designated electromagnetic field and energy are applied to the atomic nuclei such that resonance occurs and energy is discharged from the atomic nuclei.

In detail, the magnetic resonance imaging apparatus represents the strength of a magnetic resonance (MR) signal with respect to a radio frequency (RF) signal generated from a designated strength of a magnetic field as a contrast, thereby obtaining an image of a sectional region of an object.

An imaging operation using the magnetic resonance imaging apparatus causes noise of about 100 dB. The noise is caused when a coil of the MRI apparatus vibrates due to Lorentz force that is generated when an electric current is applied to a gradient coil to form a gradient magnetic field according to an imaging protocol.

A user controls a magnetic resonance imaging apparatus in an operating room provided with an operation console, and thus has a difficulty in communicating with a patient placed in a scan room during a relatively long imaging operation time.

SUMMARY

Exemplary embodiments may address at least the above problems and/or disadvantages and other disadvantages not described above. The exemplary embodiments are not required to overcome the disadvantages described above, and an exemplary embodiment may not overcome any of the problems described above.

One or more exemplary embodiments provide a magnetic resonance imaging apparatus for effectively providing visual information of an object placed in a bore, and a control method thereof.

In accordance with an aspect of an exemplary embodiment, a magnetic resonance imaging apparatus includes: a gantry provided with a bore; and an image output screen configured to output visual information to an object placed inside the bore while rotating along the bore.

The image output screen may rotate according to a line of sight of the object.

The image output screen may be provided inside the bore.

The image output screen may be provided on a table configured to transfer the object to the inside of the bore.

The image output screen may include a light source allowing the visual image to be projected onto an inside of the bore.

The image output screen may further include a support frame provided in a shape corresponding to a shape of the bore such that the light source is rotated while being supported inside the bore.

The magnetic resonance imaging apparatus may further include a controller configured to control rotation of the image output screen such that the visual information is displayed at a position corresponding to the line of sight of the object placed in the bore.

The controller may determine movement of the line of sight of the object based on change in a posture of the object that is changed according to a predetermined magnetic resonance imaging protocol.

The magnetic resonance imaging apparatus may further include a monitor configured to monitor a change in a posture of the object. The controller may analyze the line of sight of the object based on change in a posture of the object.

The monitor may monitor the change of a posture of the object based on an image of the object placed in the bore.

The controller may determine existence of an obstacle between the object and the position, at which the visual information is displayed, based on spatial information of the bore, and adjust the position if it is determined that an obstacle exists.

In accordance with an exemplary embodiment, a magnetic resonance imaging apparatus may include: a table configured to transfer an object to an inside of a bore; a support frame provided in a shape corresponding to a shape of the bore; a light source configured to allow visual information to be displayed at an inside of the bore, and rotate along the support frame; and a controller configured to control rotation of the light source according to a line of sight of the object.

The magnetic resonance imaging apparatus may further include: a guide rail provided on the support frame and configured to rotate the light source; a motor provided at an inner side of the table; and a shaft configured to deliver a rotary force of the motor to the guide rail.

The magnetic resonance imaging apparatus, further including a screen that rotates together with the light source and allows the visual information to be displayed thereon.

The visual information may be provided to obtain a functional magnetic resonance image.

In accordance with another exemplary embodiment, a method of controlling a magnetic resonance imaging apparatus having a light source to display visual information at an inside of a bore and an object placed inside the bore includes: displaying visual information at an inside of the bore; and rotating the light source according to movement of a line of sight of the object.

The method may further include: determining the movement of the line of sight of the object based on change in a posture of the object that is changed according to a predetermined magnetic resonance imaging protocol.

The method may further include analyzing change in the line of sight of the object based on change in a posture of the object.

The method may further include: obtaining an image of the object placed in the bore; and monitoring change in a posture of the object based on the obtained image of the object.

The visual information may be provided to obtain a functional magnetic resonance image.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
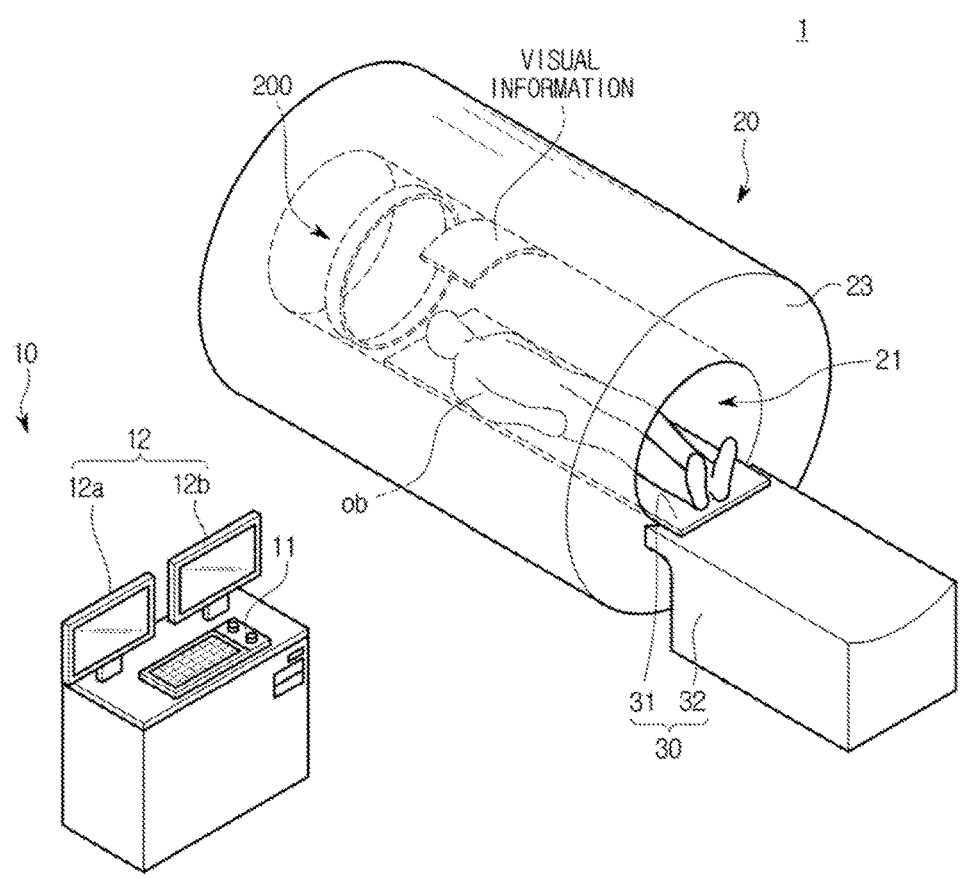
FIG. 1 is a perspective view schematically illustrating a magnetic resonance imaging apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Unless otherwise defined, it will be understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof. In addition, it will be understood that terms "part", "module" and "unit" used herein represent a unit for processing at least one function or operation, and may be implemented as software, hardware elements such as a field programmable gate array (FPGA) or an application specific integrated circuits (ASIC), or a combination of software and hardware. However, the terms of "part", "module" and "unit" are not limited to software and hardware. The terms of "part", "module" and "unit" may be configured to be provided in an addressable storage medium, or may be configured to operate one or more processors. Examples of the terms of "part", "module" and "unit" includes software elements, object-oriented software elements, class elements and task elements, processes, functions, attributes, procedures, subroutines, segments of program codes, drivers, firmware, microcode, circuit, data, database, data structure, tables, arrays and variables.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

FIG. 1 is a perspective view schematically illustrating a magnetic resonance imaging apparatus according to an exemplary embodiment.

Referring to FIG. 1, a magnetic resonance imaging apparatus 1 may include an operation console 10 allowing a user to control the magnetic resonance imaging apparatus 1 and a main body 20 configured to form a magnetic field and generate resonance with respect to atomic nuclei. In this case, 'a user' may include medical professionals, for example, a surgeon, a nurse, a medical technologist, and a medical imaging professional, and a technician who repairs a medical device, but is not limited thereto.

The operation console 10 and the main body 20 may be provided at different places, respectively. In detail, the operation console 10 may be provided in an operating room, and the main body 20 may be provided in a scan room.

The operation console 10 may include an operator panel 11 to receive a control command from a user, and a display assembly 12 to provide a user with information.

The operator panel 11 receives a control command from a user and outputs an electric signal corresponding to the input control command. The user may input or select information about an object ob, parameter information, a scan condition, a pulse sequence, and information about image combination or a different operation, by using the operator panel 11.

In addition, a user may select or input visual information that is to be provided to an object ob placed in an operating room by use of the operator panel 11. The object ob may be an organism of a human body, an animal, or any other object whose internal structure is imaged. However, the following description will be made in relation to an object ob corresponding to a human body for illustrative purposes.

The operator panel 11 may include a button input device, such as a keyboard, a push button or a membrane button, or a touch input device, such as a touch pad, but the operator panel 11 according to exemplary embodiments is not limited thereto. For example, the operator panel 11 may include other various types of input devices, for example, a track ball, a speech recognition device or a gesture recognition device.

The display assembly 12 may output a magnetic resonance image or various pieces of information needed to control the magnetic resonance imaging apparatus 1. In addition, the display assembly 12 may include a plurality of displays 12a and 12b. The plurality of displays 12a and 12b may output different magnetic resonance images, respectively. Alternatively, one of the displays 12a and 12b may display a magnetic resonance image, and another one of the displays 12a and 12b may output various pieces of information needed to control the magnetic resonance imaging apparatus 1. Although two displays 12 and 12b are illustrated in FIG. 1, a number of displays is an exemplary embodiment is not limited thereto, and the displays may include any number of displays.

The main body 20 may include a gantry 23 having a hollow cylindrical shape. The inner space of the gantry 23 is referred to as a bore 21 or a cavity. The main body 20 is provided therein with a magnet assembly to generate a magnetic field that causes resonance of atomic nuclei.

A transfer device 30 may allow an object ob to be moved to the inside of the bore 21, or to the outside of the bore 21. The transfer device 30 may include a table 31 on which the object ob is placed, and a table driver 32 configured to move the table 31 to the inside of the bore 21 or move the table 31 placed in the bore 21 to the outside of the bore 21.

An image output screen 200 may provide visual information to the object ob in the bore 21. As shown in FIG. 1, the image output screen 200 may be provided in the bore 21. For example, the image output screen 200 may be installed on an inner surface of the bore 21, and may be embodied as, for example, a screen, a monitor, a display, etc.

The image output screen 200 may provide the object ob with an image by rotating in the bore 21. A posture of the object ob in the bore 21 may be changed depending on a magnetic resonance image desired to obtain. As the posture of the object ob is changed, the field of vision of the object ob is also changed. Accordingly, in order to effectively provide image information to the object ob, the location at which an image is output in the bore 21 needs to be changed according to the posture of the object ob.

Figure 2:
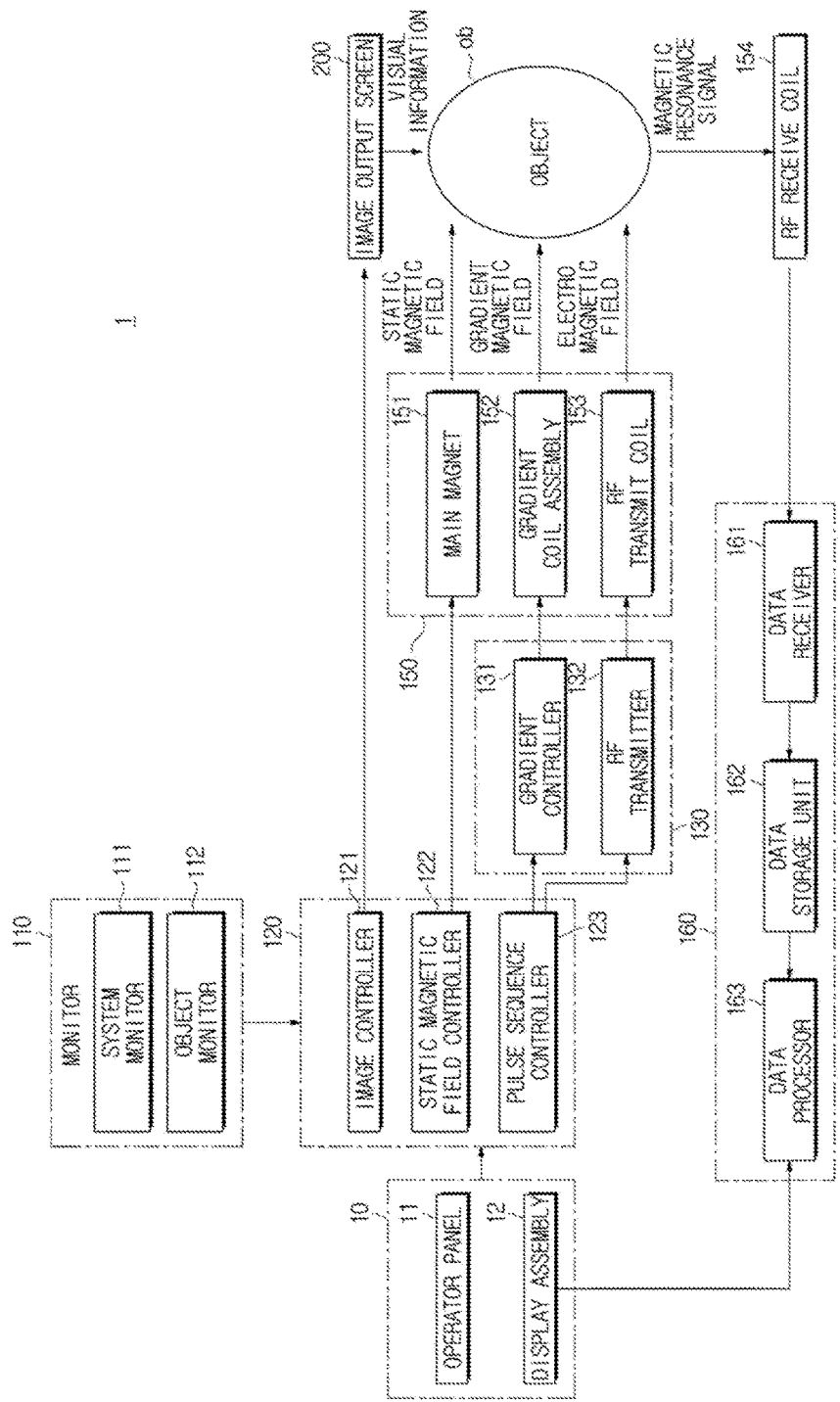
FIG. 2 is a control block diagram illustrating a magnetic resonance imaging apparatus according to an exemplary embodiment.

FIG. 2 is a control block diagram illustrating a magnetic resonance imaging apparatus according to an exemplary embodiment.

Figure 3:
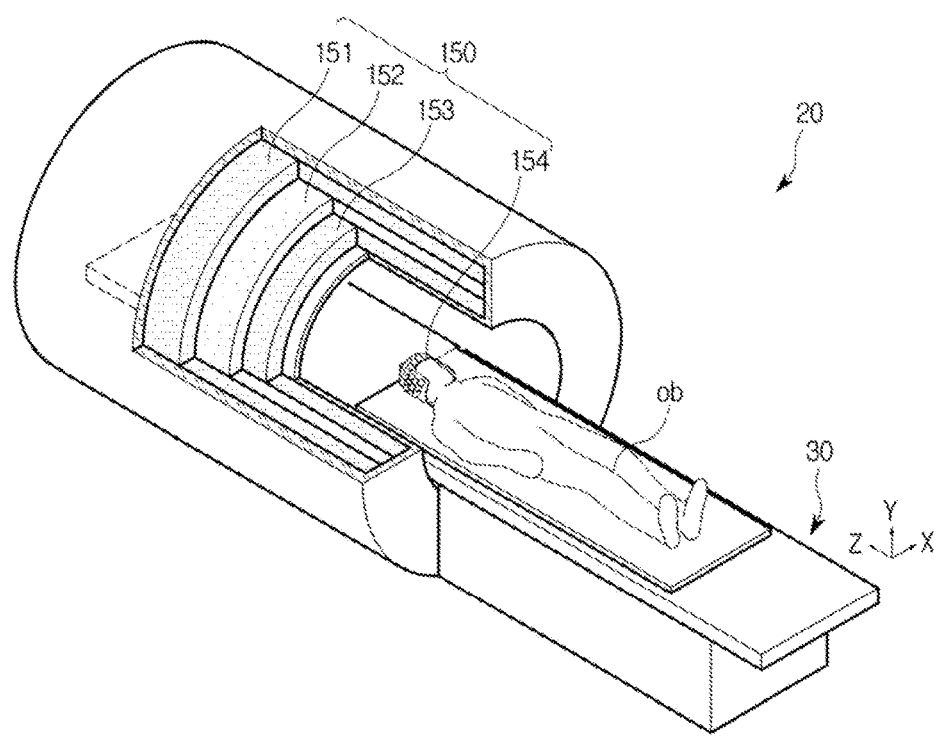
FIG. 3 is a view showing a main body of a magnetic resonance imaging apparatus including a magnet assembly according to an exemplary embodiment.

FIG. 3 is a view showing a main body of a magnetic resonance imaging apparatus including a magnet assembly.

Referring to FIGS. 1 to 3, the magnetic resonance imaging apparatus 1 includes a magnet assembly 150 forming a magnetic field and generating resonance of atomic nuclei, an image processor 160 receiving an echo signal, i.e., a magnetic resonance signal, generated from the atomic nuclei and generating a magnetic resonance image, an image output screen 200 providing an object ob with visual information, and a controller 120 controlling an overall operation of the magnetic resonance imaging apparatus 1.

The magnet assembly 150 may be provided in the main body 20. The magnet assembly 150 may include a main magnet 151 forming a static magnetic field in the inner space thereof, and a gradient coil assembly 152, i.e., gradient coils, forming a gradient magnetic field in the static magnetic field, and a radio frequency (RF) coil assembly.

The RF coil assembly includes an RF transmit coil 153 to transmit an RF pulse and an RF receive coil 154 to receive electromagnetic waves emitted from excited atomic nuclei, i.e. magnetic resonance signals. The following description will be made in relation to the RF coil assembly including the RF transmit coil and the RF receive coil, for illustrative purposes. However, the RF coil assembly according to an exemplary embodiment may be a single coil that serves as an RF receive coil and an RF transmit coil.

The RF transmit coil 153 excites atomic nuclei by applying an RF pulse, and the RF receive coil 154 receives electromagnetic wave emitted from the excited atomic nuclei, i.e. a magnetic resonance signal.

That is, when an object ob is located in the bore of the magnet assembly 150, the static magnetic field, the gradient magnetic field, and the RF pulse are applied to the object ob, and thus, atomic nuclei of the object ob are excited and a magnetic resonance signal is generated from the atomic nuclei and received by the RF receive coil 154.

The magnetic resonance imaging apparatus 1 according to an exemplary embodiment may further include a monitor 110. The monitor 110 may include a system monitor 111 monitoring the magnetic resonance imaging apparatus 1, and an object monitor 112 monitoring an object ob.

The system monitor 111 may monitor a state of a static magnetic field, a state of a gradient magnetic field, a state of an RF signal, a state of an RF coil, a state of the table 31, a state of a device configured to measure physical information of an object ob, a state of power supply, a state of a heat changer, a state of a compressor, etc.

The object monitor 112 may monitor a state of an object ob. In detail, the object monitor 112 may include an image capturing device (see 113 of FIG. 7) to observe a movement or a position of the object ob, a respiration measurer to measure respiration of the object ob, an electrocardiography (ECG) measurer to measure an electrocardiogram of the object ob, a temperature measurer to measure the temperature of the object ob, and a switch to receive an input from the object ob.

The controller 120 controls the overall operation of the magnetic resonance imaging apparatus 1 based on information received from the monitor 110. In detail, the controller 120 may include an image controller 121 to control the image output screen 200, a static magnetic field controller 122 to control the strength and direction of a static magnetic field formed by the main magnet 151, and a pulse sequence controller 123 to control the gradient coil assembly 152 and the RF transmit coil 153 by generating a pulse sequence.

In addition, the controller 120, according to a control command input through the operator panel 11 of the operation console 10, may control the magnetic resonance imaging apparatus 1 or the display assembly 12 of the operation console 10 such that information related to the magnetic resonance imaging apparatus 1 is provided to a user. In particular, the controller 120 may receive a command about a scan sequence from a user, and generate a pulse sequence according to the command.

The magnetic resonance imaging apparatus 100 according to an exemplary embodiment may further include a signal input unit 130 configured to apply a predetermined signal to the magnet assembly 150.

The signal input unit 130 includes a gradient controller 131 applying a gradient signal to the gradient coil assembly 152 and an RF transmitter 132 applying an RF signal to the RF transmit coil 153. According to the gradient controller 131 and the RF transmitter 132 controlled by the pulse sequence controller 123, the gradient magnetic field formed in the static magnetic field and the RF pulse applied to the atomic nuclei are adjusted.

Hereinafter, a detailed operation of the magnetic resonance imaging apparatus according to an exemplary embodiment of the present disclosure will be described with reference to FIGS. 1, 2, 3, 4, 5, and 6.

Figure 6:
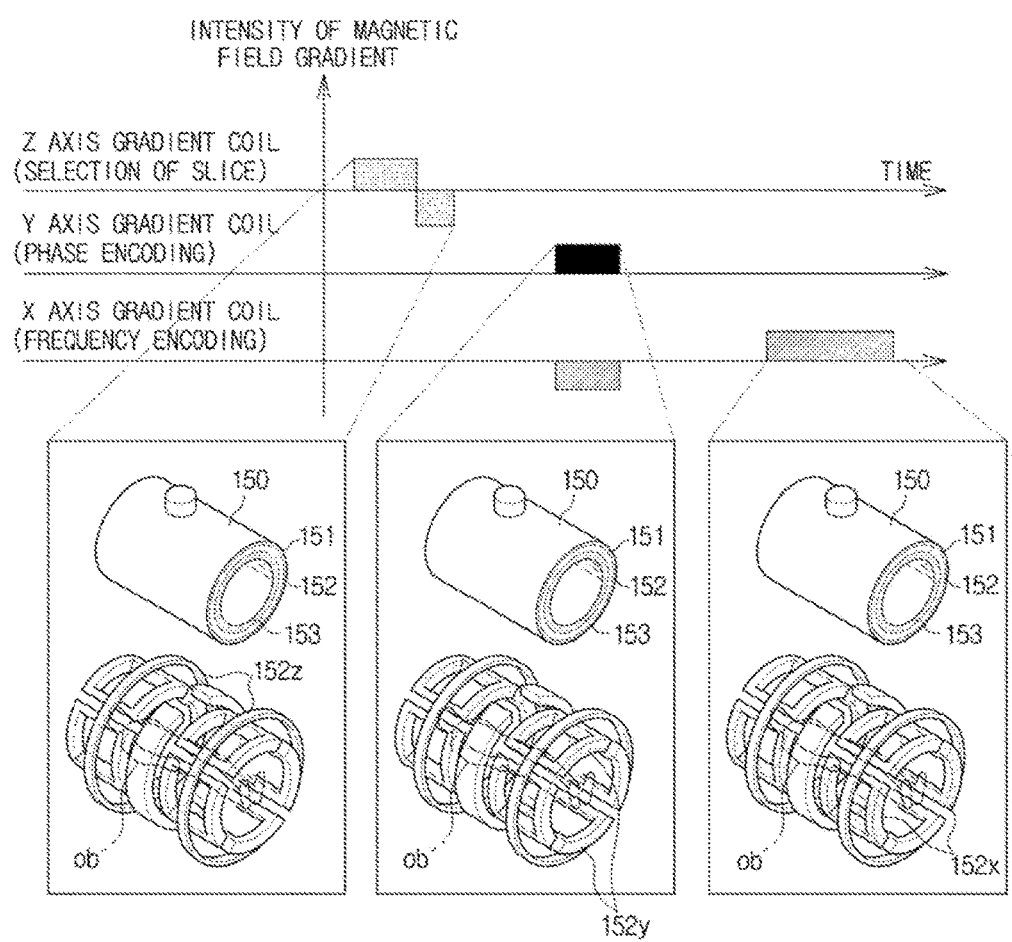
FIG. 6 is a view illustrating operations of respective gradient coils constituting a gradient coil assembly and a pulse sequence regarding operations of the respective gradient coils.

FIG. 6 is a view illustrating a pulse sequence regarding operations of respective gradient coils constituting the gradient coil assembly.

The main magnet 151 may be embodied as a coil winding around the bore 21, and when current is applied to the main magnet 151, a static magnetic field is formed in the inside of the magnet assembly 150, i.e., in the bore 21. The direction of the static magnetic field is generally parallel with the driving axis of the magnet assembly 150.

When the static magnetic field is formed in the bore 21, atomic nuclei of atoms constituting the object ob, specifically, hydrogen atoms, are arranged in the direction of the static magnetic field and execute precession with respect to the direction of the static magnetic field. The precession speed of atomic nuclei may be represented as a precession frequency, and the precession frequency may be referred to as a Larmor frequency and expressed by Equation 1 below.

$$\omega = \gamma B_0 \qquad \text{[Equation 1]}$$

Here, $\omega$ denotes a Larmor frequency, $\gamma$ denotes a proportional constant, and $B_0$ denotes the intensity of a main magnetic field which is measured in tesla (T) or gauss (G). The proportional constant $\gamma$ is different for each kind of atomic nuclei.

For example, hydrogen protons have a precession frequency of 42.58 MHz in the magnetic field of 1 T and, among elements constituting a human body, hydrogen accounts for the largest number of atoms of the human body, and thus a magnetic resonance signal may be acquired using precession of hydrogen protons during an operation of magnetic resonance imaging (MRI).

The gradient coil assembly 152 generates gradients in the static magnetic field formed in the bore 21, thus forming gradient magnetic fields.

Figure 4:
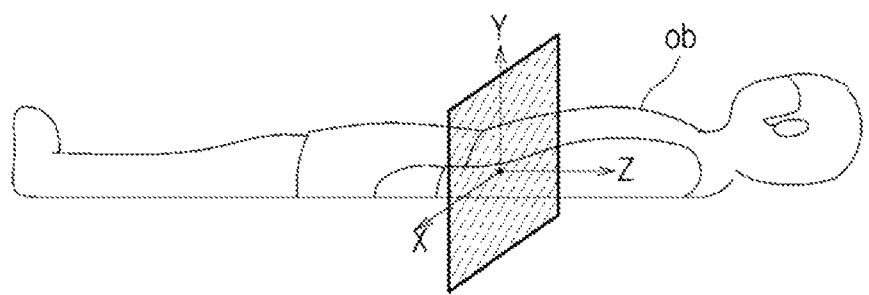
FIG. 4 is a view illustrating a position of an object with respect to an X-axis, a Y-axis and a Z-axis.

As shown in FIG. 4, an axis parallel with a lengthwise direction (or a head-to-toe direction) of the object ob, i.e., an axis parallel with the direction of the static magnetic field, may be defined as the Z-axis, an axis parallel with a lateral direction of the object ob may be defined as the X-axis, and an axis parallel with a vertical direction of the object ob may be defined as the Y-axis.

In order to acquire three-dimensional (3D) spatial information, gradient magnetic fields in directions of the X-axis, Y-axis and Z-axis may be needed. Therefore, the gradient coil assembly 152 may include three pairs of gradient coils.

Figure 5A:
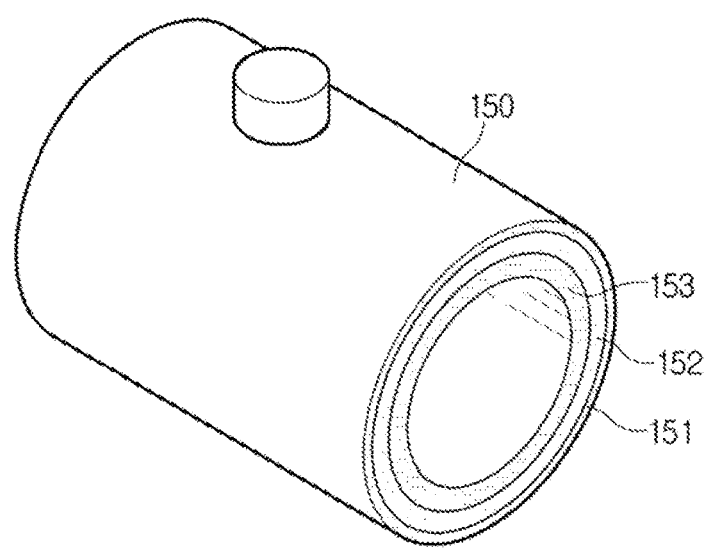
FIGS. 5A and 5B are views illustrating a structure of a magnet assembly and a structure of a gradient coil assembly.
Figure 5B:
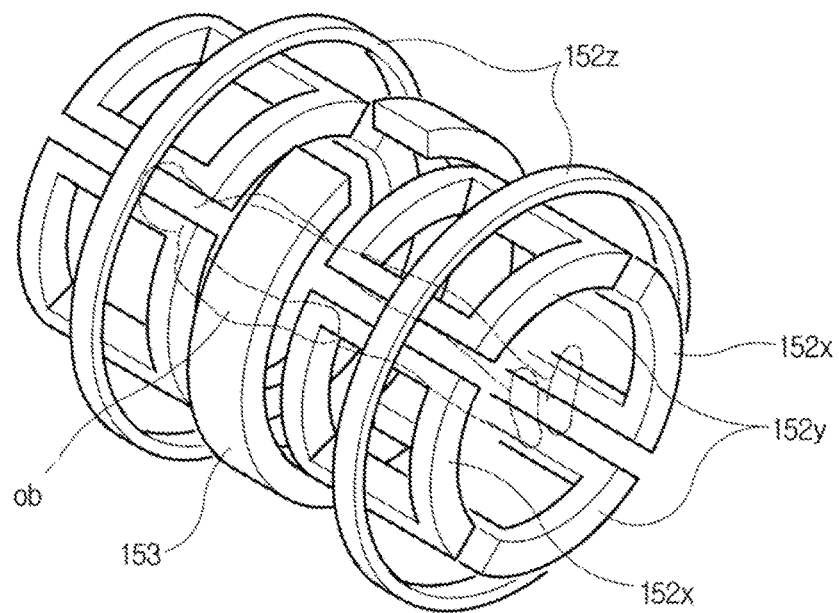

As shown in FIGS. 5 and 6, Z-axis gradient coils 152z include a pair of ring coils, and two Y-axis gradient coils 152y are respectively located above and below the object ob. Further, two X-axis gradient coils 152x are respectively located at left and right sides of the object ob.

When direct currents having opposite polarities flow in the two Z-axis gradient coils 152z in opposite directions, the magnetic field is changed in the Z-axis direction and thus a gradient magnetic field is formed. In FIG. 6, a Z-axis gradient magnetic field being formed by an operation of the Z-axis gradient coils 152z is shown as pulse sequences.

As the gradient of the gradient magnetic field formed in the Z-axis direction is increased, a slice having a smaller thickness may be selected. The Z-axis gradient coils 152z are used in slice selection.

In detail, when the gradient magnetic field is formed by flow of current along the Z-axis gradient coils 152z for a designated time, the resonance frequency is changed to a higher frequency or a lower frequency according to the size of the gradient magnetic field. When an RF signal corresponding to a specific slice is applied through the RF coil assembly 153, only protons of the specific slice resonate.

When the slice is selected through the gradient magnetic field formed by the Z-axis gradient coils 152z, all spins constituting the slice have the same frequency and the same phase and thus the respective spins are indistinguishable from one another.

When a gradient magnetic field in the Y-axis direction is formed by the Y-axis gradient coils 152y, the gradient magnetic field causes phase shift so that rows of the slice have different phases.

That is, when the Y-axis gradient magnetic field is formed, the phase of the spins of the row to which a larger gradient magnetic field is applied is changed to a higher frequency, and the phase of the spins of the row to which a smaller gradient magnetic field is applied is changed to a lower frequency. When the Y-axis gradient magnetic field is removed, phase shift of the respective rows of the selected slice occurs and thus the respective rows have different phases such that the rows may be distinguished from one another.

As described above, the gradient magnetic field formed by the Y-axis gradient coils 152y is used in phase encoding. In FIG. 6, a Y-axis gradient magnetic field being formed by operation of the Y-axis gradient coils 152y is shown as pulse sequences.

The slice is selected through the gradient magnetic field formed by the Z-axis gradient coils 152z, and the rows constituting the selected slice are distinguished from one another by different phases through the gradient magnetic field formed by the Y-axis gradient coils 152y. However, the respective spins constituting each row have the same frequency and the same phase, and are thus indistinguishable from one another.

When a gradient magnetic field in the X-axis direction is formed by the X-axis gradient coils 152x, the X-axis gradient magnetic field causes the spins constituting each row to have different frequencies so that the respective spins are distinguishable from one another. As described above, the gradient magnetic field formed by the X-axis gradient coils 152x is used in frequency encoding.

As described above, the gradient magnetic fields formed by the Z-axis, Y-axis and X-axis gradient coils 152x, 152y, 152z execute encoding of spatial positions of the respective spins, i.e., spatial encoding, through slice selection, phase encoding and frequency encoding.

The gradient coil assembly 152 is connected to the gradient controller 130, and the gradient controller 130 applies a driving signal to the gradient coil assembly 152 according to a control signal transmitted from the pulse sequence controller 123 and generates gradient magnetic fields. Therefore, the gradient controller 130 may include three drive circuits corresponding to the three pairs of gradient coils 152x, 152y and 152z of the gradient coil assembly 152.

Lorentz force is generated when current is applied to the gradient coil assembly 152 in order to generate gradient magnetic fields. The Lorentz force causes vibration of the coils, and such vibration causes noise generated during magnetic resonance imaging. A noise level varies according to shapes and sizes of the gradient magnetic fields through imaging techniques, and relates to characteristics of gradient magnetic field coils.

When the atomic nuclei arranged by a magnetic field execute precession at the Larmor frequency as described above, a magnetization vector sum of several atomic nuclei may be represented as net magnetization M.

A Z-axis component of the net magnetization M is not measurable, and thus only net magnetization on X-Y plane $M_{xy}$ may be detected. Therefore, in order to acquire a magnetic resonance signal, the net magnetization M needs to be present on the X-Y plane through excitation of the atomic nuclei. In order to excite the atomic nuclei, an RF pulse tuned to the Larmor frequency of the atomic nuclei needs to be applied to the static magnetic field.

The RF coil assembly is connected to the RF transmitter 132, and the RF transmitter 132 applies a drive signal to the RF transmit coil 153 according to a control signal transmitted from the pulse sequence controller 123 and transmits the RF pulse.

The RF transmitter 132 may include a modulation circuit modulating a high frequency output signal into an RF pulse signal, and an RF power amplifier amplifying the RF pulse signal.

In addition, the RF coil assembly may control the RF transmit coil 153 to receive a magnetic resonance signal. The RF transmit coil 153 is connected to the image processor 160, and the image processor 160 receives data regarding the magnetic resonance signal generated from the atomic nuclei and generates a magnetic resonance image by processing the data regarding the magnetic resonance signal.

In detail, the image processor 160 includes a data receiver 161 and a data processor 163 generating a magnetic resonance image by processing the data received by the data receiver 161.

The data receiver 161 includes a pre-amplifier amplifying the magnetic resonance signal received by the RF receive coil 154, a phase detector receiving the magnetic resonance signal transmitted from the pre-amplifier and detecting a phase, and an analog-to-digital (A/D) converter converting an analog signal acquired through phase detection into a digital signal. Further, the data receiver 161 transmits the magnetic resonance signal converted into the digital signal to a data storage unit 162.

A data space constructing a two-dimensional (2D) Fourier space is formed in the data storage unit 162, and when data obtained by scanning the object ob is stored, the data processor 163 reconfigures the image of the object ob by performing 2D inverse Fourier transform upon the stored data in the 2D Fourier space. The reconfigured image is displayed on the display assembly 12.

To acquire a magnetic resonance signal from atomic nuclei, a spin echo pulse sequence may be used. When the RF transmit coil 153 applies RF pulses, when a second RF pulse is transmitted after an appropriate time interval Δt from application of a first RF pulse, strong transverse magnetization of the atomic nuclei may occurs after the time interval Δt lapses, and a magnetic resonance signal may be acquired from the transverse magnetization. This method is referred to as a spin echo pulse sequence, and the time interval Δt time taken to generate the magnetic resonance signal after application of the first RF pulse is referred to as time echo (TE).

A flip degree of protons may be represented as an angle by which the protons move from an axis where the protons are located before being flipped, and be represented as a 90 degree RF pulse, a 180 degree RF pulse, etc., according to the flip degree of the protons.

Magnetic resonance imaging may last more than 30 minutes, and in some cases, more than one hour. The image output screen 200 may provide the object ob with predetermined visual information during the magnetic resonance imaging.

There is no limitation to the visual information output through the image output screen 200. In an example, the image output screen 200 may output visual information for communication between the object ob in the bore 21 and the user who controls the magnetic resonance imaging apparatus 1. As described above, due to the noise occurring due to the Lorentz force generated when an electric current is applied to the gradient coils, it may be difficult to communicate between the object ob in the scan room and the user in the operating room. Accordingly, the user may transfer predetermined information to the object ob through the image output screen 200, and the object ob may transfer predetermined information to the user through an input device, e.g., by operating a remote controller.

In another example, the image output screen 200 may output imaging information related to the magnetic resonance imaging. For example, the progress of the magnetic resonance imaging and information about a region that is being imaged by the magnetic resonance imaging may be output so that the imaging information about the magnetic resonance imaging is provided to the object ob in the bore 21. Since imaging information related to the magnetic resonance imaging is provided to the object ob, the object ob (or a patient) may feel less boredom and anxiety. Also, since information about a region being imaged is provided to the object ob, the object ob may remain still with respect to the region being imaged and thus a clear image of the region may be obtained.

In a still another example, the image output screen 200 may provide the object ob with an image content to reduce boredom. In this case, the image content may include, for example, television (TV) programs and movies.

In a still another example, the image output screen may output visual information for obtaining a magnetic resonance image. That is, the image output screen 200 may output visual information for performing a functional magnetic resonance imaging (fMRI).

Examples of the fMRI may include a brain imaging. When the object ob recognizes visual information, the brain of the object ob is activated according to the visual information. In this case, the activated area of the brain consumes more oxygen than other areas, and thus has an increased blood flow. By measuring blood oxygen level dependent (BOLD) due to the increase in blood flow, an activation pattern of the brain function may be imaged.

That is, the image output screen 200 may output an image configured to give a stimulus to the brain during the magnetic resonance imaging as the visual information provided to the object ob.

Hereinafter, the image output screen 200 included in the magnetic resonance imaging apparatus according to an exemplary embodiment will be described with reference to FIGS. 7 and 8.

Figure 7:
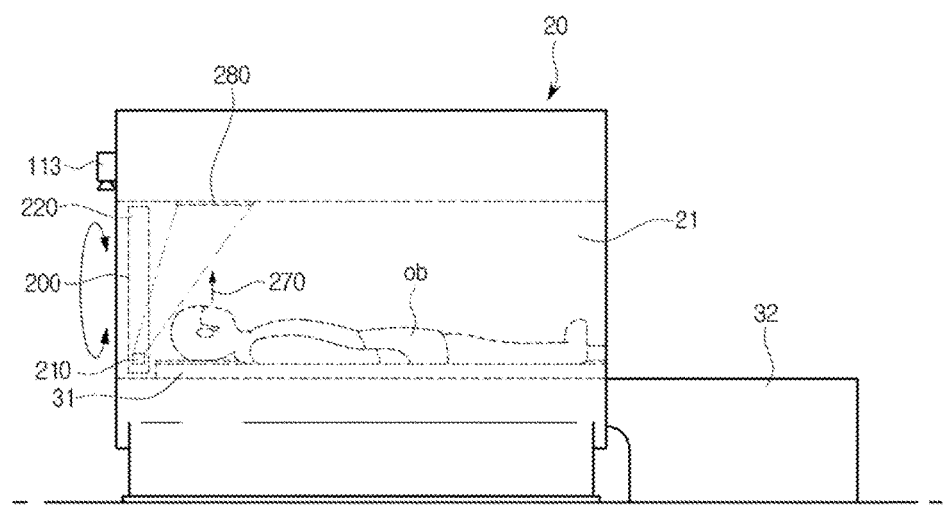
FIG. 7 is a view showing a magnetic resonance imaging apparatus provided with an image output screen according to an exemplary embodiment.
Figure 8:
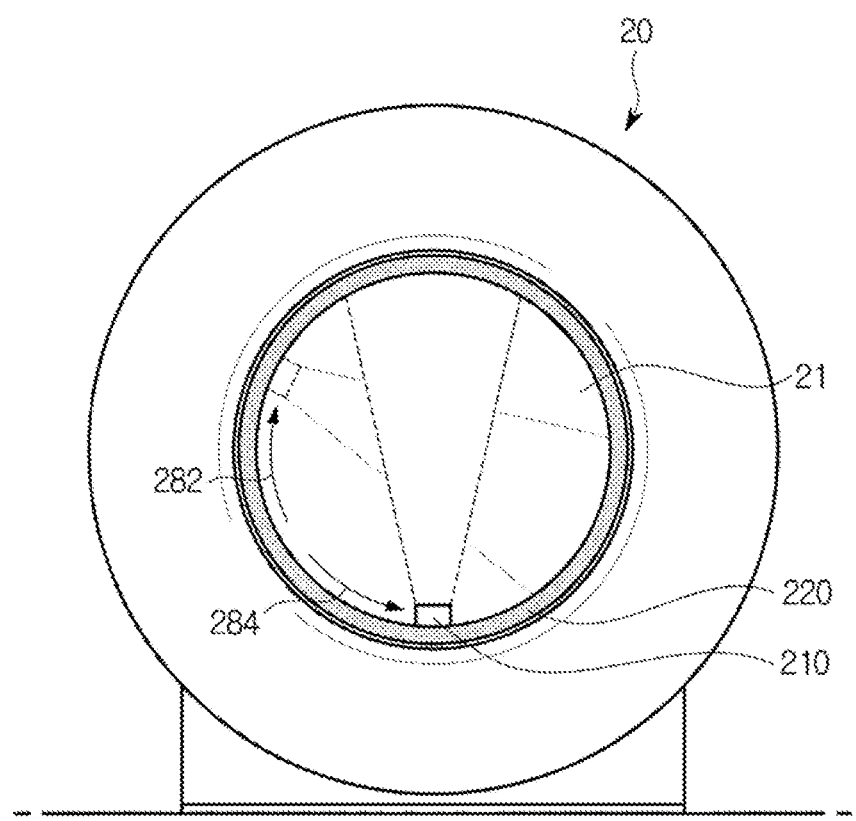
FIG. 8 is a view illustrating of a magnetic resonance imaging apparatus for describing rotation of an image output screen according to an exemplary embodiment.

FIG. 7 is a view showing a magnetic resonance imaging apparatus provided with an image output screen according to an exemplary embodiment, and FIG. 8 is a view illustrating a magnetic resonance imaging apparatus for describing rotation of the image output screen according to an exemplary embodiment.

Referring to FIGS. 3, 7 and 8, the image output screen 200 is provided in the bore 21 to provide the object ob placed in the bore 21 with visual information. The image output screen 200 may include a light source 210 provided to display visual information and a support frame 220.

The light source 210 may output visual information at a portion of a surface of the bore 21 corresponding to a control signal of the image controller 121. The light source 210 may include a light emitting diode (LED) that is not affected by the magnetic field, and may further include a lens to adjust a focus of light being emitted.

Figure 9:
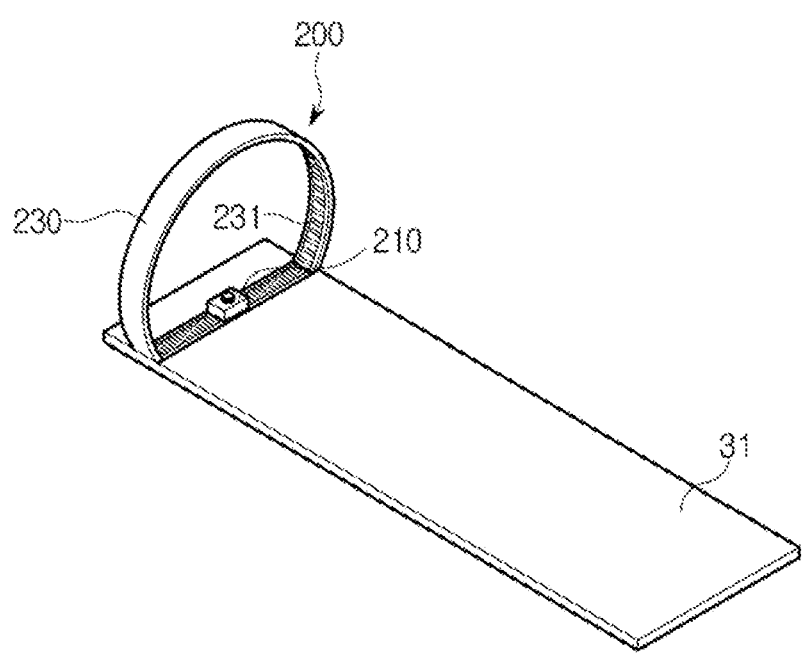
FIG. 9 is a perspective view illustrating a table of a transfer device provided with an image output screen according to an exemplary embodiment.
Figure 10:
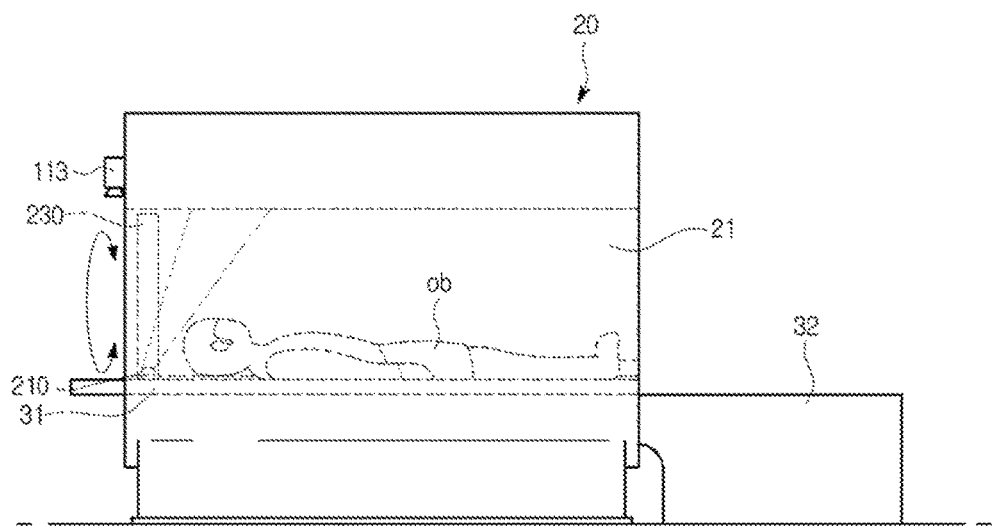
FIG. 10 is a view illustrating a magnetic resonance imaging apparatus provided with an image output screen according to an exemplary embodiment.

The support frame 220 supports the light source 210. The support frame 220 may be provided as a ring along the bore 21, as shown in FIGS. 7 and 8. The light source 210 may be rotated in the bore 21 along the support frame 220 in a clockwise direction 282 or a counterclockwise direction 284. For example, the support frame 220 is provided with a guide rail (see 231 in FIG. 9) at an inner side of the support frame 220. As the guide rail rotates, the light source 210 may rotate in the bore 21 along the support frame 220.

The image controller 121 may control the image output screen 200 such that visual information set in advance or selected by a user is provided to the object ob in the bore 21. In detail, the image controller 121 generates a control signal to control the light source 210 such that a predetermined piece of visual information is displayed at a side of the bore 21.

In order to effectively provide the object ob with visual information, the visual information needs to be displayed at a region 280 corresponding to the line of sight 270 of the object ob. Accordingly, the image controller 121 may adjust the position of the image output screen 200 such that visual information may be effectively provided.

Accordingly, the image controller 121 may adjust the position of the image output screen 200 based on the line of sight 270 of the object ob. If the posture or position of the object ob is changed, the line of sight 270 of the object ob is changed. Therefore, in order to effectively transmit the visual information to the object ob, the position of the image output screen 200 needs to be adjusted such that visual information is displayed at a region 280 corresponding to the line of sight 270 of the object ob.

The image controller 121 may rotate the light source 210 such that visual information is displayed at a region 280 corresponding to the line of sight 270 of the object ob.

In detail, the image controller 121 may adjust the position of the light source 210 according to a predetermined imaging protocol. The magnetic resonance imaging apparatus 1 acquires a magnetic resonance image by capturing an image of the object ob according to a predetermined imaging protocol. When a posture or position of the object ob is changed according to the imaging protocol for the magnetic resonance imaging, the image controller 121 may change the position of the light source 121 according to the movement of the line of sight 270 of the object ob caused by the change in the posture or position of the object ob.

According to an exemplary embodiment, when the object ob positioned to have a lateral direction (or a shoulder-to-shoulder direction) in parallel to the X-axis changes the posture or position to have the shoulder-to-shoulder direction to be parallel to the Y-axis according to a predetermined imaging protocol, the direction of a line of sight 270 of the object ob may be changed to a direction toward a lateral side of the bore 21 from a direction toward an upper side of the bore 21. As the posture of the object ob is changed according to a predetermined imaging protocol, the image controller 121 controls the image output screen 200 such that the light source 210 is rotated by a predetermined angle along the support frame 220 and thus visual information is displayed at a lateral side of the bore 21 corresponding to the direction of the line of sight 270 of the object ob.

According to another exemplary embodiment, when the image controller 121 may adjust the position of the light source 210 based on the posture of the object ob acquired by the target monitor 112. In this case, the object monitor 112 may acquire the posture of the object ob from the image capturing device 113 provided on the main body 20.

The image capturing device 113 acquires an image of the object ob by photographing the object ob being moved to the inside of the bore 21. The image capturing device 113 may be installed outside the bore 21 so as not to be affected by the magnetic field formed in the bore 21, and the image capturing device 113 may be installed at a position above the head of the object ob when the object ob is placed in the bore 21 such that a top view including a facial region of the object ob is captured.

The image capturing device 113 may include a wide viewing angle camera. In order to acquire a posture or position of the object ob, the inside of the bore 21 needs to be photographed. However, due to the magnetic field formed in the bore 21, the image capturing device 113 is installed outside the bore 21, and the image capturing device 113 may include a wide viewing angle camera having an angle of view wider than normal cameras, thereby photographing the object ob placed in the bore 21. The angle of view of the image capturing device 113 may vary with the length of the magnet assembly 150.

The object monitor 112 determines a motion of the object ob by analyzing an image of the object ob acquired by the image capturing device 113. The image acquired by the image capturing device 113 may be a still image captured at a predetermined time interval, or a moving image captured in real time.

In detail, the image captured by the image capturing device 113 is transmitted to the object monitor 112, and the object monitor 112 acquires a current posture of the object ob from the transmitted image, and compares the current posture with a previous posture, thereby monitoring a motion of the object ob. In this case, the posture acquisition and comparison of the object ob may be performed using an edge detection algorithm. However, the posture acquisition and comparison of the object ob is not limited thereto, and may be implemented in various image analysis algorithms.

The image controller 121 determines a change in the posture of the object ob based on movement of the object ob monitored by the object monitor 112, and determines whether a line of sight 270 of the object ob is changed according to the change in the posture of the object ob.

If it is determined that a line of sight 270 of the object ob is changed, the image controller 12 may control the light source 210 such that visual information is displayed on a certain region in the bore 21 corresponding to the position of the changed line of sight 270.

Although the image output screen 200 is illustrated as being provided inside the bore 21, exemplary embodiments are not limited thereto. Hereinafter, the image output screen 200 of the magnetic resonance imaging apparatus in accordance with an exemplary embodiment will be described with reference to FIGS. 9, 10, 11, and 12 in detail.

In the following description, details of parts identical or substantially similar to those of the previous embodiments will be omitted in order to avoid redundancy.

Referring to FIGS. 9 to 12, the image output screen 200 may be provided with the transfer device 30. In detail, the image output screen 200 may be provided with the table 31 so as to be moved to the inside or outside of the bore 21 together with the object ob.

That is, a support frame 230 may be provided on the table 31, and a lower portion of the support frame 230 may be integrally formed with the table 31, and an upper portion of the support frame 230 may be provided in a shape corresponding to the shape of the bore 21. Also, the support frame 230 is provided with a guide rail 231 at an inner side of the support frame 230. As the guide rail 231 rotates, the light source 210 may rotate along the support frame 220.

Figure 11:
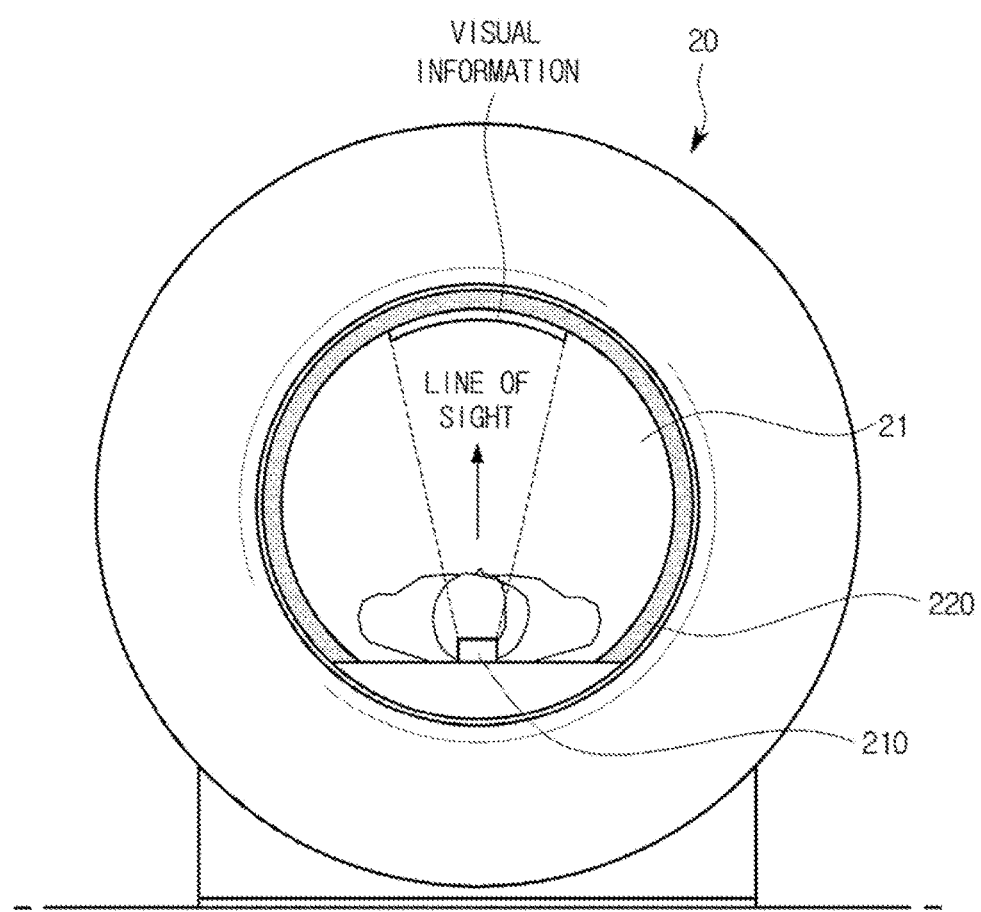
FIGS. 11 and 12 are views illustrating a movement of a light source of an image output screen according to an exemplary embodiment.

As described above, the light source 210 may rotate according to a line of sight of the object ob. For example, as shown in FIG. 11, when a line of sight of the object ob is directed to an upper side of the bore 21, the light source 210 emits light toward the upper side of the bore 21 to display visual information at the upper side of the bore 21.

Figure 12:
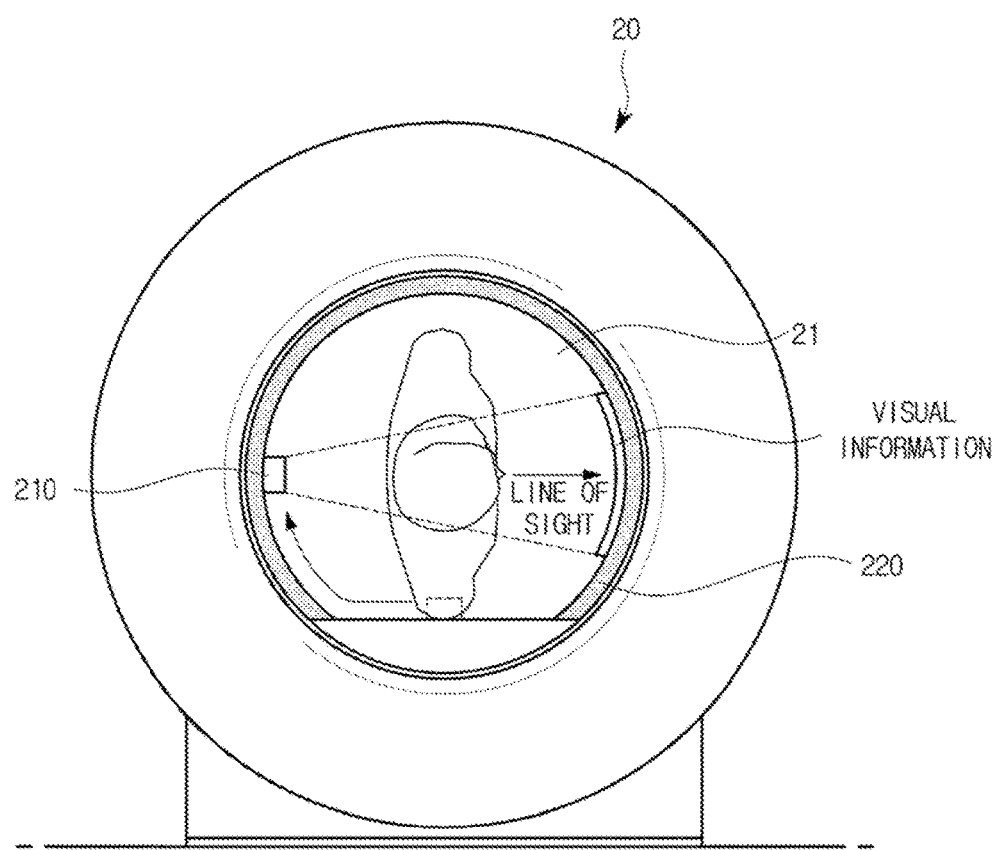

Referring to FIG. 12, when the object ob changes the posture of the object ob, the direction of a line of sight of the object ob is moved from a direction toward the upper side of the bore 21 to a direction toward the lateral side of the bore 21. As the line of sight of the object ob is moved to the lateral side of the bore 21, the light source 210 rotates together with the support frame 230 according to the movement direction of the line of sight.

Figure 13:
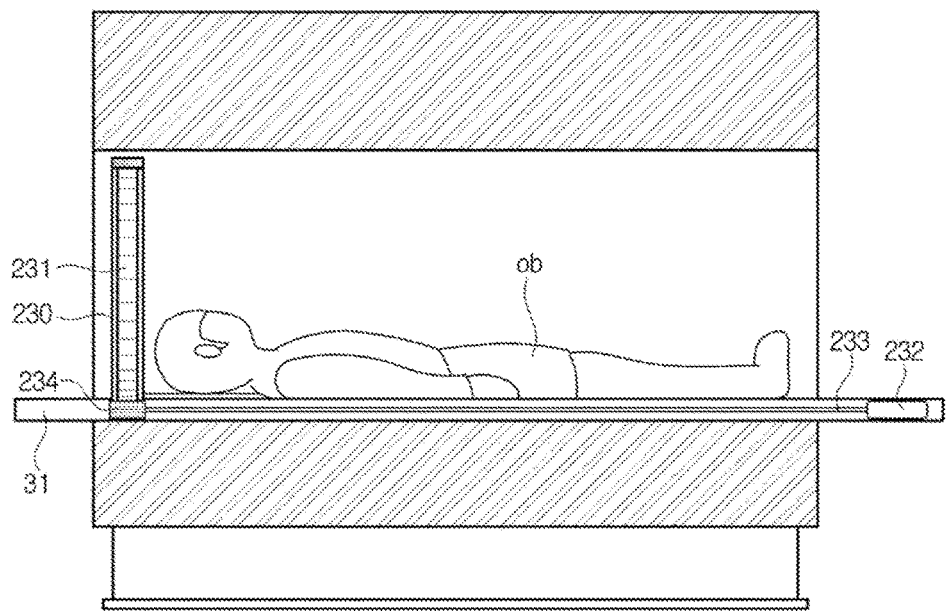
FIG. 13 is a schematic view illustrating a driving device configured to move a light source according to an exemplary embodiment.

FIG. 13 is a schematic view illustrating a driving device configured to move a light source according to an exemplary embodiment.

The image output screen 200 may further include a driving apparatus to move the light source. In this case, the driving apparatus may be spaced apart from the main body 20 to reduce influence from a magnetic field and prevent distortion of a magnetic resonance signal. For example, the driving apparatus may be provided on the transfer device 30, e.g., the table 31.

In detail, referring to FIG. 13, a motor 232, a shaft 233 and a gear 234 may be provided on the table 31 to rotate the guide rail 231. When the guide rail 231 rotates, the light source 210 coupled to the guide rail 231 may rotate along the support frame 230.

The motor 232 may rotate according to control of the image controller 121. The motor 232 may include a stepping motor whose rotation angle is adjustable so that rotation of the light source 210 may be precisely adjusted.

The shaft 233 transmits a rotary force of the motor 232 to the guide rail 231. To this end, a first end of the shaft 233 is coupled to a rotary shaft of the motor 232, and a second end of the shaft 233 is provided with the gear 234 connected to the guide rail 231.

Referring to FIG. 13, the motor 232 may be spaced apart from the main body 20, thereby reducing influence on the motor 232 by the magnetic field, and preventing distortion of a magnetic resonance signal due to driving of the motor 232.

Figure 14:
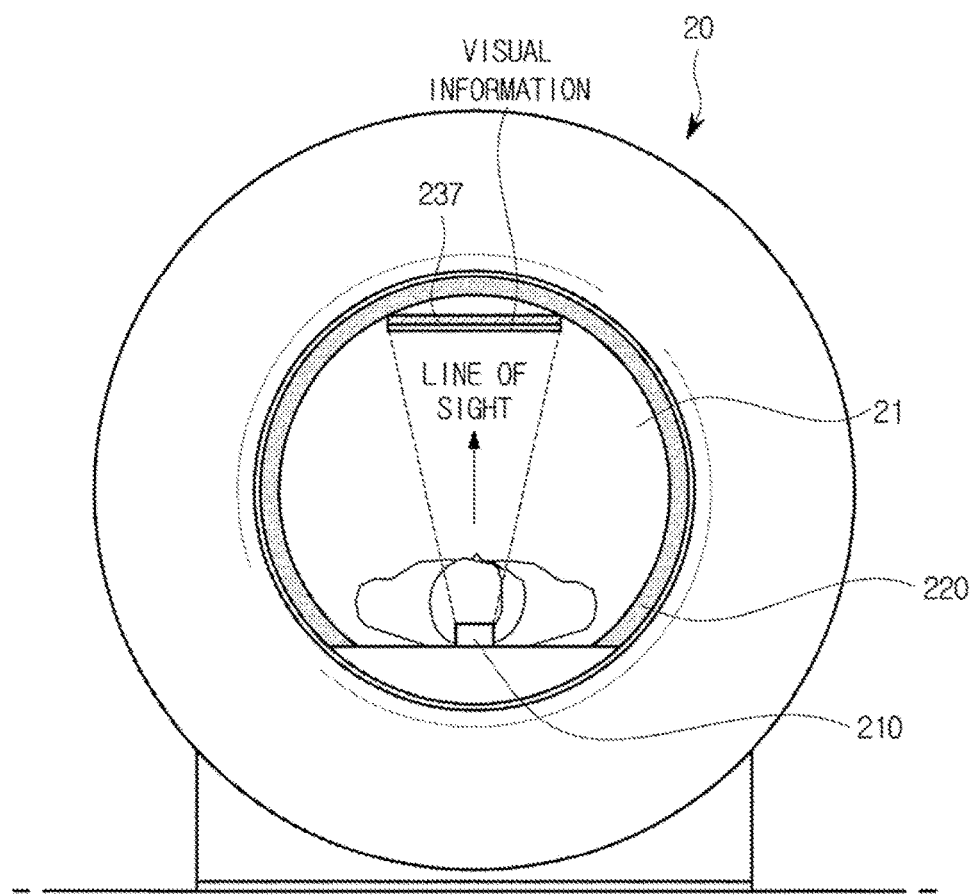
FIGS. 14 and 15 are views illustrating a screen on which visual information is displayed according to exemplary embodiments.
Figure 15:
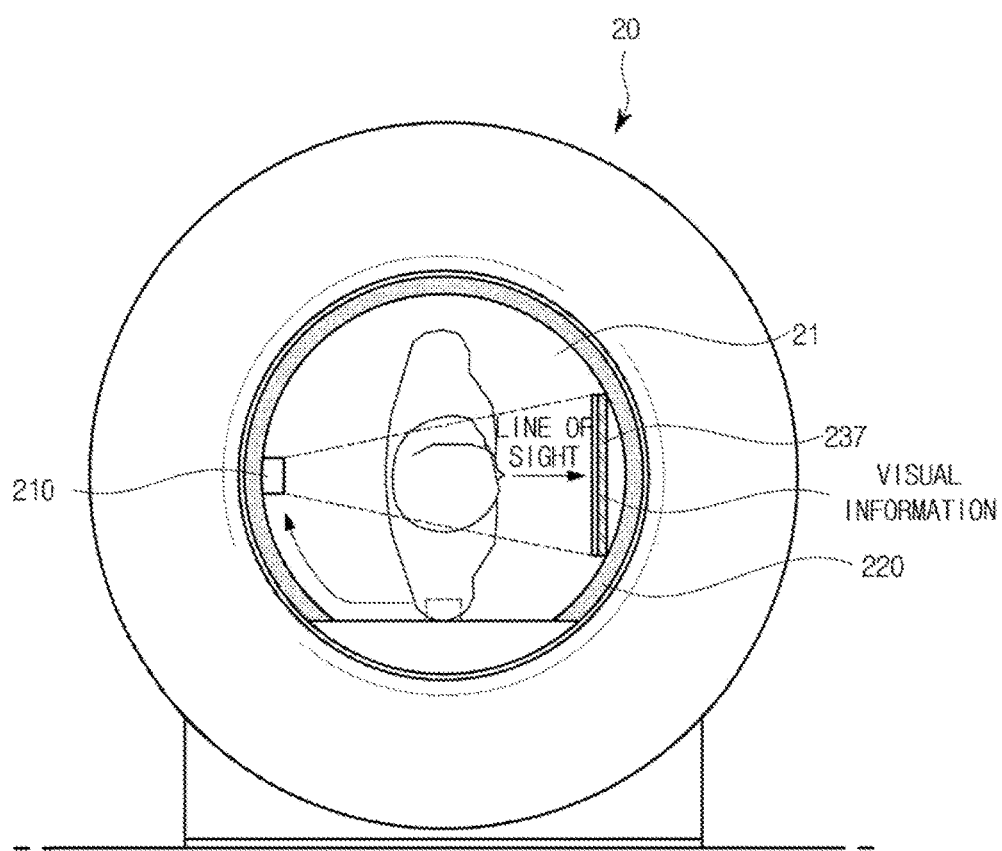

FIGS. 14 and 15 are views illustrating a screen on which visual information is displayed according to exemplary embodiments.

The image output screen 200 may further include a screen 237 onto which visual information is projected. In detail, referring to FIGS. 14 and 15, the screen 237 may be provided at a position corresponding to the light source 210.

The screen 237 is provided at the position corresponding to the light source 210 so that the visual information is more clearly provided.

In addition, the screen 237 may be coupled to the guide rail 231 provided on the support frame 230 so as to rotate together with the light source 210 as shown in FIGS. 14 and 15.

The image controller 121 may adjust the position at which visual information is displayed, e.g., the position of the screen 237, based on spatial information of the bore 21. The spatial information may be position information about various devices present in the bore 21. For example, the spatial information may include position information of a respiration measurer to measure respiration of the object ob, position information of an electrocardiography (ECG) measurer to measure an electrocardiogram of the object ob, position information of a temperature measurer to measure the temperature of the object ob, position information of a switch to receive an input from the object ob, and position information of an RF receive coil.

In detail, the visual information is generated by projecting light emitted from the light source 210 onto the bore 21. Accordingly, if the light emitted from the light source 210 is blocked by an obstacle, the visual information is not projected onto the bore 21. Accordingly, the image controller 121 may manage spatial information in the bore 21, and adjust the position of the light source 210 to prevent the light emitted from the light source 210 from being blocked by the obstacle.

For example, when the RF receive coil 154 is provided on the head of the object ob as shown in FIG. 3, the light emitted from the light source 210 may be blocked by the RF receive coil 154. If the light is blocked by the RF receive coil 154, visual information is not projected onto the bore 21 so that the position of the light source 210 may be adjusted to prevent light from being blocked by the RF receive coil 154.

Hereinafter, a method of controlling a magnetic resonance imaging apparatus in accordance with an exemplary embodiment will be described with reference to FIGS. 16 and 17 in detail.

Figure 16:
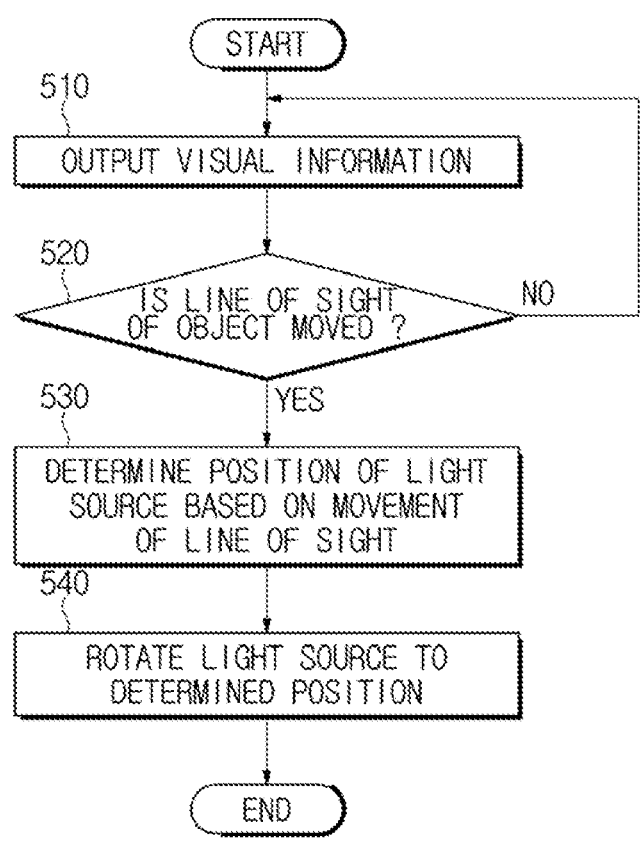
FIG. 16 is a flowchart showing a control method of a magnetic resonance imaging apparatus according to an exemplary embodiment.

FIG. 16 is a flow chart showing a control method of a magnetic resonance imaging apparatus according to an exemplary embodiment.

Referring to FIG. 16, the light source 210 outputs visual information to the inside of the bore 21 (operation 510). In detail, the light source 210 may output a predetermined piece of visual information according to a control signal of the image controller 121, and the visual information is projected onto a side of the bore 21.

The magnetic resonance imaging apparatus 1 may allow a user to communicate with the object ob in the bore 21 through visual information, or to transmit imaging information related to a magnetic resonance imaging to the object ob. In addition, the visual information may be information used to provide the brain of the object ob with a predetermined stimulation.

The magnetic resonance imaging apparatus 1 determines movement of a line of sight of the object ob (operation 520). The magnetic resonance imaging apparatus 1 acquires a magnetic resonance image by imaging the object ob according to a predetermined imaging protocol. In this case, based on the change in the posture or position of the object ob according to the imaging protocol for the magnetic resonance imaging, it is determined whether the line of sight of the object ob is moved.

If it is determined that the line of sight of the object ob is not moved ("No" in operation 520), the method returns to operation 510 to output visual information to the inside of the bore 21.

If it is determined that the line of sight of the object ob is moved ("Yes" in operation 520), the light source 210 determines the position to which the light source 210 is moved, based on the movement of the line of sight of the object ob (operation 530). In detail, the magnetic resonance imaging apparatus 1 determines a position to which the light source 210 is to be moved so that visual information is displayed at a region corresponding to the moved line of sight of the object ob.

The magnetic resonance imaging apparatus 1 rotates the light source 210 to the determined position (operation 540).

Figure 17:
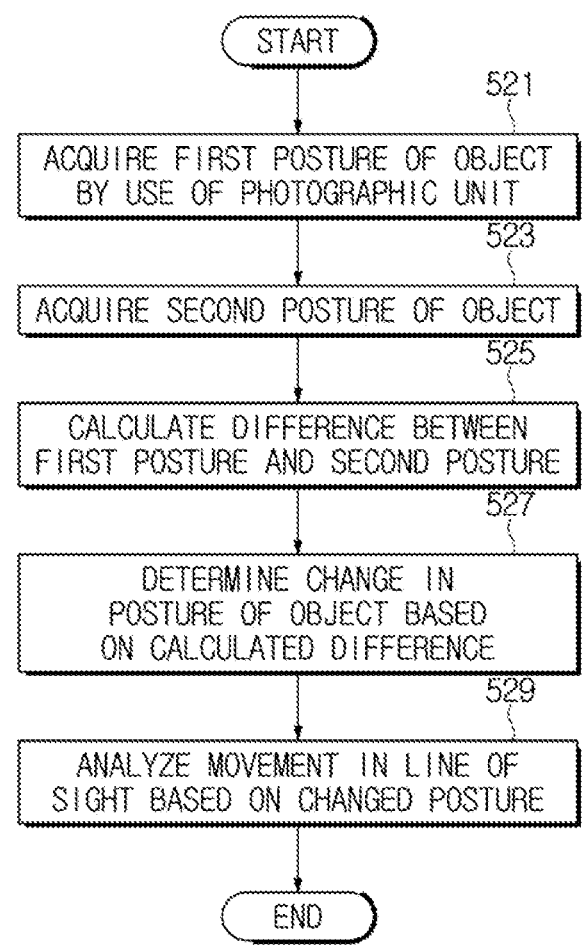
FIG. 17 is a flowchart illustrating a method of analyzing movement of a line of sight of an object according to an exemplary embodiment.

FIG. 17 is a flow chart illustrating a method of analyzing movement of a line of sight of an object.

Referring to FIG. 17, the magnetic resonance imaging apparatus 1 acquires a first posture of the object ob by using the image capturing device 113 (operation 521). To this end, the magnetic resonance imaging apparatus 1 acquires an image of the object ob placed in the bore 21 through the image capturing device 113, and acquires a first posture from the image of the object ob by use of, for example, the edge detection method.

In this case, the image of the object ob may be a moving image, or a still image. In addition, the image capturing device 113 is installed at an outside of the bore 21 so as not to interfere with the magnetic field formed in the bore 21. The image capturing device 113 may be implemented using a wide viewing angle camera such that an image representing a movement of the object ob is acquired.

In addition, the magnetic resonance imaging apparatus 1 performs image capturing at a time interval or in real time, to acquire an image of the object ob such that a second posture of the object ob is acquired from the acquired image (operation 523).

The magnetic resonance imaging apparatus 1 compares the first posture with the second posture of the object ob to determine the degree of change in the posture of the object ob, and calculates a difference between the first posture and the second posture (operation 525).

The magnetic resonance imaging apparatus 1 determines the change in the posture of the object ob based on the calculated difference (operation 527), and based on the change in the posture, analyzes the movement in the line of sight (operation 529).

According to the magnetic resonance imaging apparatus and the control method according to exemplary embodiments, visual information can be displayed while being movable according to movement of a line of sight of the object, thereby effectively displaying visual information to the object.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. A magnetic resonance imaging (MRI) apparatus comprising:
    a gantry including a bore having a ring shape; and
    an image output screen configured to rotate along the ring shape of the bore and output visual information to an object placed in the bore,
    wherein the image output screen comprises:
        a support frame having a shape corresponding to the ring shape of the bore;
        a light source configured to display the visual information inside the bore and rotate along the support frame; and
        a guide rail provided on the support frame and configured to rotate the light source along the support frame.

2. The magnetic resonance imaging apparatus of claim 1, wherein the image output screen is configured to rotate according to a line of sight of the object.

3. The magnetic resonance imaging apparatus of claim 1, wherein the image output screen is provided inside the bore.

4. The magnetic resonance imaging apparatus of claim 1, wherein the image output screen is provided on a table configured to transfer the object to in and out the bore.

5. The magnetic resonance imaging apparatus of claim 1, wherein the light source is further configured to project the visual information inside the bore.

6. The magnetic resonance imaging apparatus of claim 1, further comprising:
    a controller configured to control a rotation of the image output screen such that the visual information is displayed at a position corresponding to a line of sight of the object placed in the bore.

7. The magnetic resonance imaging apparatus of claim 6, wherein the controller is configured to determine a movement of the line of sight of the object based on a change in a posture of the object according to a magnetic resonance imaging protocol, which is being executed.

8. The magnetic resonance imaging apparatus of claim 6, further comprising:
    a monitor configured to monitor a change in a posture of the object,
    wherein the controller is configured to determine the line of sight of the object based on the change in the posture of the object.

9. The magnetic resonance imaging apparatus of claim 8, wherein the monitor is configured to monitor the change in the posture of the object based on an image of the object placed in the bore.

10. The magnetic resonance imaging apparatus of claim 9, wherein the monitor comprises an image capturing device configured to photograph the object placed in the bore.

11. The magnetic resonance imaging apparatus of claim 10, wherein the image capturing device is positioned outside of the bore.

12. The magnetic resonance imaging apparatus of claim 10, wherein the image capturing device comprises a wide angle camera having a wide viewing angle.

13. The magnetic resonance imaging apparatus of claim 10, wherein the image of the object comprises at least one of a still image captured at a time interval and a moving image captured in real time.

14. The magnetic resonance imaging apparatus of claim 6, wherein the controller is configured to make a determination as to a presence of an obstacle between the object and the position at which the visual information is displayed, based on spatial information of the bore, and adjust the position based on a result of the determination.

15. A magnetic resonance imaging (MRI) apparatus comprising:
    a table configured to transfer an object to a bore of a magnetic resonance (MR) scanner;
    a support frame having a shape corresponding to a ring shape of the bore;

a light source configured to allow visual information to be displayed inside the bore, and rotate along the support frame;
a guide rail provided on the support frame and configured to rotate the light source along the support frame; and
a controller configured to control a rotation of the light source according to a line of sight of the object.

16. The magnetic resonance imaging apparatus of claim 15, further comprising:
a motor provided at the table; and
a shaft configured to transmit a rotary force of the motor to the guide rail.

17. The magnetic resonance imaging apparatus of claim 15, further comprising:
an image output screen configured to rotate together with the light source and display the visual information.

18. The magnetic resonance imaging apparatus of claim 15, wherein the visual information is provided to obtain a functional magnetic resonance image.

19. A method of controlling a magnetic resonance imaging (MRI) apparatus comprising:
displaying a visual information inside of a bore of a magnetic resonance (MR) scanner using a light source disposed in the bore; and
rotating the light source along a support frame according to movement of a line of sight of an object positioned inside the bore for imaging using a guide rail, and
wherein the support frame has a shape corresponding to a ring shape of the bore; and
wherein the guide rail provided on the support frame and configured to rotate the light source along the support frame.

20. The method of claim 19, further comprising:
determining the movement of the line of sight of the object based on a change in a posture of the object according to a magnetic resonance imaging protocol being executed by the MR scanner.

21. The method of claim 19, further comprising:
determining a change in the line of sight of the object based on a change in a posture of the object.

22. The method of claim 21, further comprising:
obtaining an image of the object placed in the bore; and
monitoring the change in the posture of the object based on the obtained image of the object.

23. The method of claim 19, wherein the visual information is provided to obtain a functional magnetic resonance image.

* * * * *